US009125641B2

(12) United States Patent
Bookwalter et al.

(10) Patent No.: US 9,125,641 B2
(45) Date of Patent: Sep. 8, 2015

(54) THREE DIMENSIONAL TILT RACHET WITH SELF RETAINING MECHANISM

(71) Applicant: SYMMETRY MEDICAL MANUFACTURING, INC, Warsaw, IN (US)

(72) Inventors: John Bookwalter, Putney, VT (US); Kevin Redmond, Fort Lauderdale, FL (US)

(73) Assignee: Specialty Surgical Instrumentation, Inc, Antioch, TN (US)

( * ) Notice: Subject to any disclaimer, the term of this patent is extended or adjusted under 35 U.S.C. 154(b) by 0 days.

(21) Appl. No.: 14/089,975

(22) Filed: Nov. 26, 2013

(65) Prior Publication Data
US 2014/0171748 A1 Jun. 19, 2014

Related U.S. Application Data

(60) Provisional application No. 61/730,536, filed on Nov. 28, 2012.

(51) Int. Cl.
*A61B 1/32* (2006.01)
*A61B 17/02* (2006.01)
*A61B 19/00* (2006.01)

(52) U.S. Cl.
CPC ............... *A61B 17/0293* (2013.01); *A61B 1/32* (2013.01); *A61B 17/02* (2013.01); *A61B 19/26* (2013.01); *A61B 2019/267* (2013.01)

(58) Field of Classification Search
CPC . A61B 1/32; A61B 17/0293; A61B 2019/267
USPC .......... 600/201, 210, 213, 225–229, 231–234
See application file for complete search history.

(56) References Cited

U.S. PATENT DOCUMENTS 4,467,971 A * 8/1984 Schuman ...................... 241/215
6,042,542 A * 3/2000 Koros et al. ................... 600/231
(Continued)

FOREIGN PATENT DOCUMENTS

SU 1388003 A1 4/1988

OTHER PUBLICATIONS

International Search Report, ISA/FIPS, Feb. 27, 2014.

*Primary Examiner* — Eduardo C Robert
*Assistant Examiner* — Tessa Matthews
(74) *Attorney, Agent, or Firm* — AKC Patents, LLC; Aliki K. Collins (57) ABSTRACT

A ratchet assembly for multi-dimensional movement and placement of a retractor blade includes a retractor blade holder, a housing member, a rotating indexer and a self-retaining locking mechanism. The retractor blade holder is shaped and dimensioned to receive a stem of a retractor blade and includes a locking mechanism that enables selective lateral adjustment of the retractor blade relative to the retractor blade holder. The retractor blade holder is mated to the housing member and is vertically pivotable with respect to the housing member to enable selective vertical pivoting adjustment of the retractor blade relative to the housing member. The rotating indexer is mated to the housing member, and the housing member is rotatable with respect to the rotating indexer so that the retractor blade holder, the housing member and the retractor blade are able to selectively rotate about the longitudinal axis of the rotating indexer. The rotating indexer is shaped and dimensioned to mount onto a rim of a surgical support. The self-retaining locking mechanism simultaneously locks or unlocks the position of the housing member relative to the rotating indexer and the position of the rotating indexer and the entire ratchet assembly onto the rim of the surgical support.

8 Claims, 9 Drawing Sheets

(56) References Cited

U.S. PATENT DOCUMENTS

| | | | |
|---|---|---|---|
| 6,620,097 B1 * | 9/2003 | Bookwalter et al. | 600/231 |
| 2002/0152833 A1 * | 10/2002 | Phillips | 74/575 |
| 2003/0065251 A1 * | 4/2003 | Feng et al. | 600/229 |
| 2008/0071145 A1 * | 3/2008 | Bjork et al. | 600/227 |
| 2009/0216087 A1 * | 8/2009 | Bjork | 600/201 |

* cited by examiner

THREE DIMENSIONAL TILT RACHET WITH SELF RETAINING MECHANISM

CROSS REFERENCE TO RELATED CO-PENDING APPLICATIONS

This application claims the benefit of U.S. provisional application Ser. No. 61/730,536 filed on Nov. 28, 2012 and entitled THREE DIMENSIONAL TILT RACHET WITH SELF RETAINING MECHANISM, which is commonly assigned and the contents of which are expressly incorporated herein by reference.

FIELD OF THE INVENTION

The present invention relates to a three-dimensional tilt ratchet for holding a surgical retractor blade and more particularly to a three-dimensional tilt ratchet with a self-retaining mechanism for attaching the ratchet to a support structure.

BACKGROUND OF THE INVENTION

Figure 1:
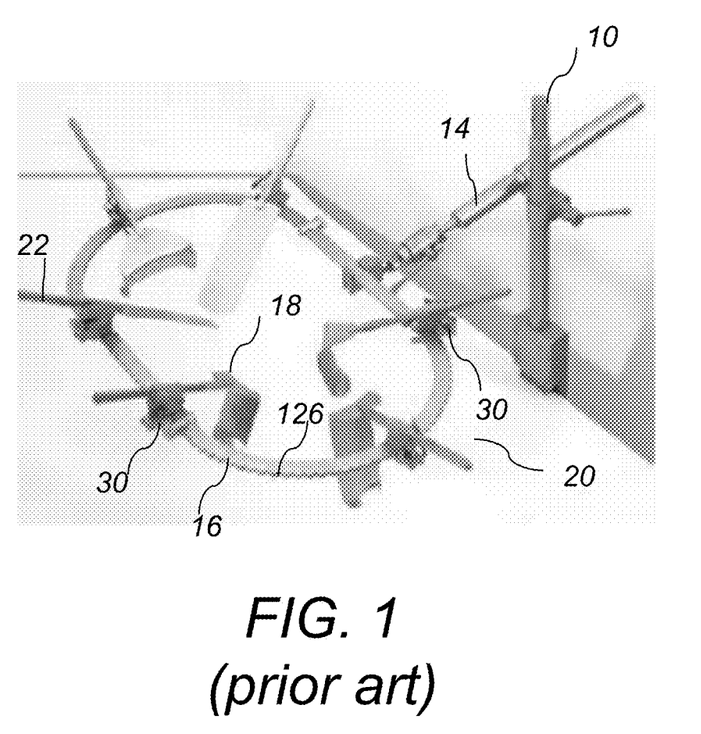
FIG. 1 depicts a schematic view of a retractor system with a prior art three-dimensional tilt ratchet assembly.

In surgical operations of the chest or abdomen, it is often necessary to use a retraction apparatus to retain tissue away from the operative site. Referring to FIG. 1, a retraction apparatus includes a housing member 30 configured to lock onto a circumferential ring 16 located above the operative site 20. To maintain the ring 16 in a fixed position, the ring is connected to a support post 10 adjacent to the operation site 20. An extension arm 14 is attached to the support post 10 for supporting the circumferential retention ring 16. A retraction blade 18 is placed within the housing member 30 and is used for grabbing the tissue around the surgical incision. The housing member 30 also includes a ratcheting mechanism and/or a tilting mechanism to draw the retraction blade 18 away from the incision, thereby effecting the pulling away and/or lifting of the tissue around the incision to expose the desired surgical area. Examples of such retractor systems are disclosed in U.S. Pat. No. 6,620,097, the contents of which are expressly incorporated herein by reference. These prior art retractor systems enable the tilt and the movement of the retractor blade in and out of the wound site. They can also provide angular adjustment, or rotation, of the retractor blade without having to remove the ratchet from the ring.

In some cases it is desirable to mount the three-dimensional tilt ratchet (3D-ratchet) on various type of support structures or to move the 3D-ratchet to different positions around the support structure. Accordingly it is desirable to have an easy mechanism for mounting and dismounting the multi-position tilt ratchet onto various types of support structures. It is also desirable to be able to lock the 3D-ratchet onto the support structure and still allow for positional changes around the support structure while the ratchet remains locked.

SUMMARY OF THE INVENTION

The present invention provides a three-dimensional tilt ratchet with a self-retaining mechanism for attaching the ratchet to a support structure.

In general, in one aspect, the invention features a ratchet assembly for multi-dimensional movement and placement of a retractor blade. The ratchet assembly includes a retractor blade holder, a housing member, a rotating indexer and a self-retaining locking mechanism. The retractor blade holder is shaped and dimensioned to receive a stem of a retractor blade and includes a locking mechanism that enables selective lateral adjustment of the retractor blade relative to the retractor blade holder. The retractor blade holder is mated to the housing member and the retractor blade holder is vertically pivotable with respect to the housing member to enable selective vertical pivoting adjustment of the retractor blade relative to the housing member. The rotating indexer is mated to the housing member, and the housing member is rotatable with respect to the rotating indexer so that the retractor blade holder, the housing member and the retractor blade are able to selectively rotate about the longitudinal axis of the rotating indexer. The rotating indexer is shaped and dimensioned to mount onto a rim of a surgical support. The self-retaining locking mechanism simultaneously locks or unlocks the position of the housing member relative to the rotating indexer and the position of the rotating indexer and the entire ratchet assembly onto the rim of the surgical support.

Implementations of this aspect of the invention may include one or more of the following features. The self-retaining locking mechanism comprises a spring-loaded lever, a spring-loaded key and a spring loaded retention clip. The spring loaded key interfaces with and engages a circumferential slot formed on the rotating indexer to lock the position of the housing member relative to the rotating indexer, and to lock the position of the rotating indexer and the entire ratchet assembly onto the rim of the surgical support with the spring loaded retention clip. Depressing of the spring loaded lever disengages the spring loaded key from the circumferential slot and propels the rotating indexer forward and thereby simultaneously unlocks the position of the housing member relative to the rotating indexer, and unlocks the rotating indexer and the entire ratchet assembly from the rim of the surgical support by opening the spring loaded retention clip. The spring loaded retention clip comprises a hook-shaped clip that is shaped and dimensioned to lock the position of the rotating index and the entire ratchet assembly onto the rim of the surgical support and is connected to a front lower portion of the rotating indexer via a spring loaded hinge. The spring-loaded hinge includes a pin configured to be inserted within an opening formed in the front lower portion of the rotating indexer, and a spring. The self retaining locking mechanism further includes a set of at least two springs and wherein the set of the at least two springs is activated when the spring loaded key disengages from the circumferential slot and the at least two springs propel the rotating indexer forward. The rotating indexer further includes a slot shaped and dimensioned to enable the ratchet assembly to be attached to the rim of the surgical support, and a plurality of indents extending circumferentially about the rotating indexer and being shaped and dimension to set and maintain the angular position of the housing member relative to the rotating indexer. A locking pin extends from the housing member and engages one of the plurality of indents of the rotating indexer for maintaining the angular position of the housing member relative to the rotating indexer. The indents are arranged at increments of 10 to 30 degrees.

In general, in another aspect, the invention features a method for providing multi-dimensional movement and placement of a retractor blade including the following. Providing a retractor blade holder shaped and dimensioned to receive a stem of a retractor blade, the retractor blade holder comprising a locking mechanism that enables selective lateral adjustment of the refractor blade relative to the retractor blade holder. Next, providing a housing member to which the retractor blade holder is mated. The retractor blade holder is vertically pivotable with respect to the housing member to enable selective vertical pivoting adjustment of the retractor blade relative to the housing member. Next, providing a rotating indexer mated to the housing member. The housing member is rotatable with respect to the rotating indexer so that the retractor blade holder, the housing member and the retractor blade are able to selectively rotate about the longitudinal axis of the rotating indexer. The rotating indexer is shaped and dimensioned to mount onto a rim of a surgical support. Finally, providing a self-retaining locking mechanism that simultaneously locks or unlocks the position of the housing member relative to the rotating indexer and the position of the rotating indexer onto the rim of the surgical support.

Among the advantages of this invention may be one or more of the following. The three-dimensional tilt ratchet is used for holding a surgical retractor blade and provides flexibility in positioning and orienting the blade during surgical procedures. The three-dimensional tilt ratchet can be used with various types of support structures and can support different types of retractor blades. The three-dimensional tilt also provides several positioning options of the retractor blade.

The details of one or more embodiments of the invention are set forth in the accompanying drawings and description bellow. Other features, objects and advantages of the invention will be apparent from the following description of the preferred embodiments, the drawings and from the claims.

BRIEF DESCRIPTION OF THE DRAWINGS

Referring to the figures, wherein like numerals represent like parts throughout the several views.

DETAILED DESCRIPTION OF THE INVENTION

Figure 2A:
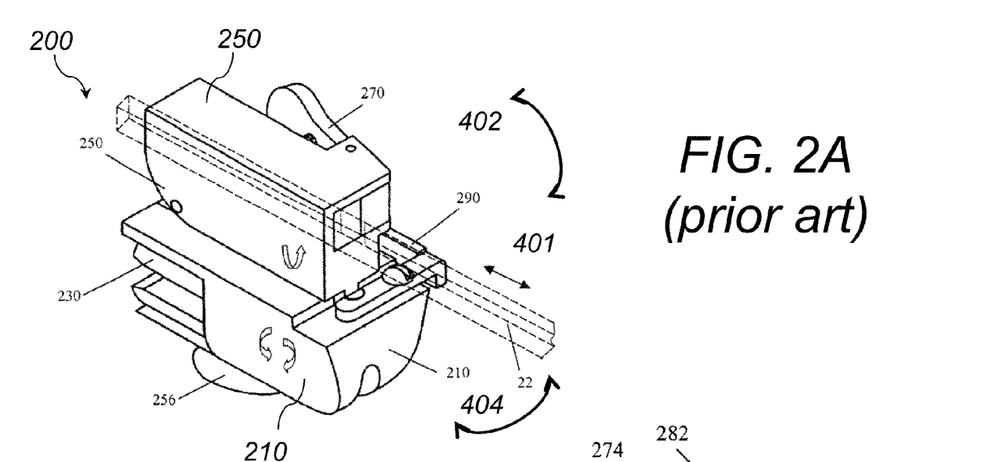
FIG. 2A is a perspective view of a prior art three-dimensional tilt ratchet assembly in the non-tilted configuration.
Figure 2B:
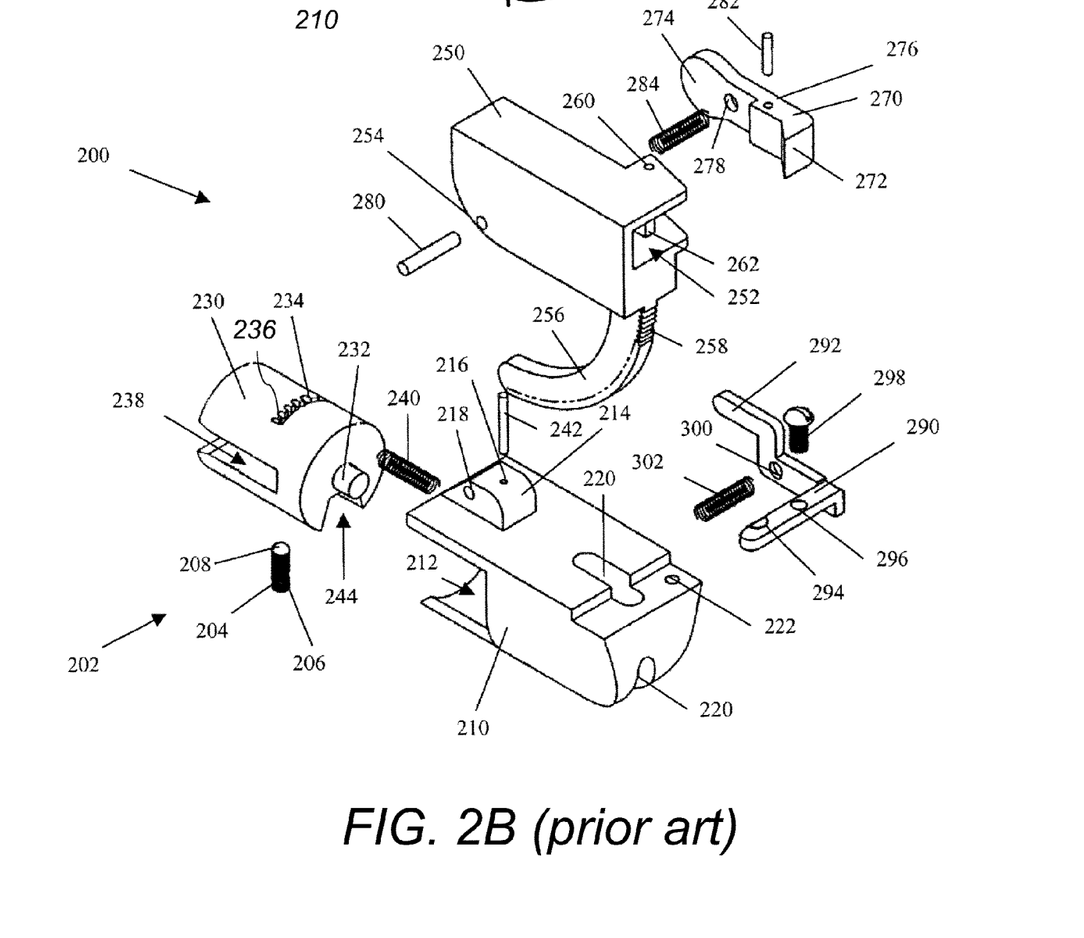
FIG. 2B is an exploded view of the three-dimensional tilt ratchet assembly of FIG. 2A.

Referring to FIG. 2A and FIG. 2B, there is shown a prior art surgical retractor assembly as disclosed in U.S. Pat. No. 6,620,097, the contents of which are incorporated herein by reference. Prior art retractor assembly 200 includes a housing member 210 configured to hold a rotating indexer 230. A retractor blade holder 250 is pivotally connected to housing member 210 and is adapted to retain a retractor blade 18 with an attached elongate ratcheted stem 22 similar to the one depicted in FIG. 1. As the bidirectional arrow 401 suggests, the retractor blade 18 and attached elongate ratcheted stem 22 can be moved towards or away from the retractor blade holder 250 and fixed at this specific distance with spring-biased lever 270. Refractor blade holder 250 can also be vertically pivoted up and down as indicated by the arrow 402, that is, towards or away from housing member 210 to effect the vertical position of the retractor blade 18, and fixed in place with ratchet release bar 290. Finally, rotating indexer 230 and housing member 210 are rotatable (as indicated by arrow 404) with respect to one another to effect angular adjustment of the retractor blade 18 and attached stem 22. Housing member 210 is rotatable about the longitudinal axis of rotating indexer 230.

Housing member 210 includes an opening 212 configured in size and shape to receive rotating indexer 230, and a ramp 214 for creating a hinged or pivoting connection with retractor blade holder 250. The rotating indexer 230 includes a protrusion 232 over which is placed indexer spring coil 240. As shown, indexer receiving opening 212, rotating indexer 230, and protrusion 232 can be substantially cylindrical in shape and sized so that rotating indexer 230 is capable of rotating within housing member 210 without interference. Inside housing member 210 is a coil receiving notch (not shown) for receiving the free end of indexer spring coil 240. Indexer spring coil 240 is longer than protrusion 232 such that rotating indexer 230 is subject to a spring force in a lateral direction when rotating indexer 230 and indexer spring coil 240 are placed within housing member 210 and seated within the coil receiving notch, thereby enabling rotating indexer 230 to be slightly moved in or out of the housing member 210 against the spring force bias with manual manipulation.

A slot 238 on rotating indexer 230 enables the ratchet mechanism 200 to be attached to a circumferential ring 16. A ball plunger assembly 202 comprising a spring actuated plunger 204 and ball 208 is provided within the rotating indexer 230 for achieving an interference fit between the tilt ratchet mechanism 200 and ring 16 for securing the ratchet mechanism 200 to the ring 16. The plunger 204 and attached ball 208 are configured to extend through an aperture (not shown) within rotating indexer 230 so that a portion of the ball plunger assembly 202 protrudes from housing member 210 through slot 238 of the rotating indexer 230. In this manner, ball plunger assembly 202 also helps maintain rotating indexer 230 within housing member 210. When ring 16 is placed into slot 238 of rotating indexer 230, ball plunger assembly 202 can be seated against one of the indentations 126 on the ring 16, locking the tilt ratchet mechanism 200 onto the ring. Removal of the tilt ratchet mechanism 200 can easily be accomplished by applying a force against the rotating indexer 230 to depress the plunger 204 and unseat the ball 208 from the indentation 126 so that the ring 16 can slide out of slot 238.

To enable rotating indexer 230 to rotate and maintain an angular position within housing member 210, a plurality of indents 234 are provided on rotating indexer 230 as shown in FIG. 2B. The plurality of indents 234 are connected by a common trench 236 and extend in a row in a circumferential direction along a surface of the rotating indexer 230, with each of the indents 234 being spaced approximately 10 degrees apart from an adjacent indent. An individual indent 234 can be engaged by an indexer pin 242 mounted through a longitudinally extending indexer pin bore 216 on housing member 210 as shown in FIG. 2B. The spring force exerted by indexer spring coil 240 enables rotating indexer 230 to be easily pushed in or out so that indexer pin 242 can stay in a specific indent 234 or slide into another indent 234. As configured, the rotating indexer 230 can be rotated in increments of approximately 10 degrees up to about 30 degrees to the left or to the right with respect to the plane of the circumferential ring 16, to the left or right of plane perpendicular to midpoint of rotating indexer 230. The retraction force applied to the retractor blade 18 in FIG. 1 will push the rotating indexer 230 into the encapsulating housing member 210 and allow the indexer pin 242 to engage one of the indents 234, locking the rotating indexer 230 in the desired angle. Thus, the tilt ratchet mechanism 200 of the present invention can be rotated or angled up to about 30 degrees to the left or right with respect to the plane of the ring 16. Such features permit a closer duplication of the original function of a toed-in hand held retractor and greatly facilitates deployment of retractor blades in deep wounds and against bone. In addition, blade exchange and blade removal for the wound is also facilitated without removing the tilt ratchet mechanism 200 from the ring 16.

Figure 3A:
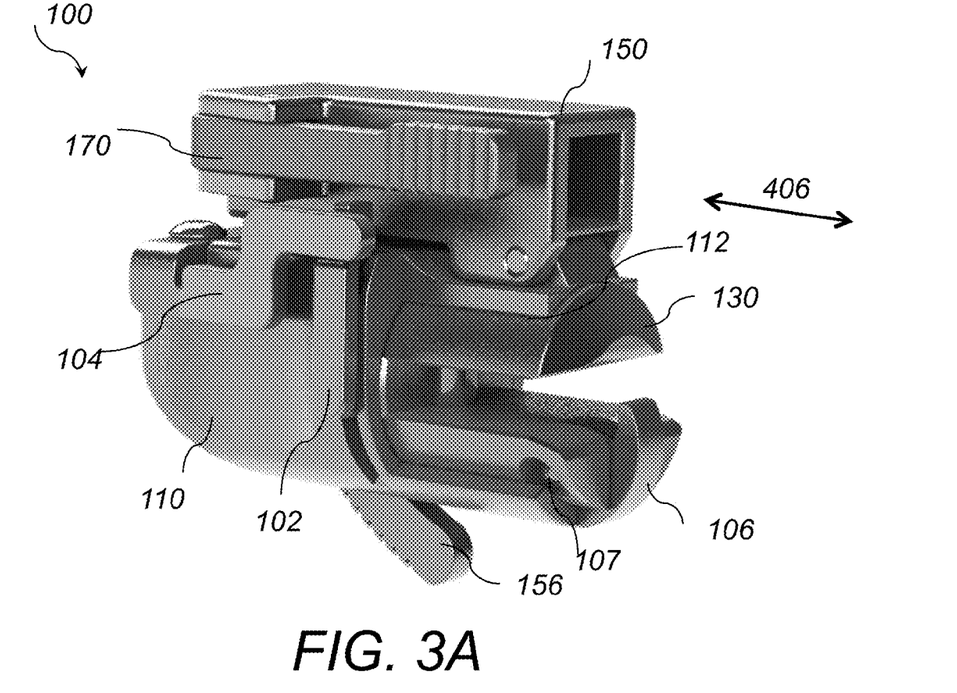
FIG. 3A is a perspective view of a three-dimensional tilt ratchet assembly according to this invention in the non-tilted configuration and "closed" position.
Figure 3B:
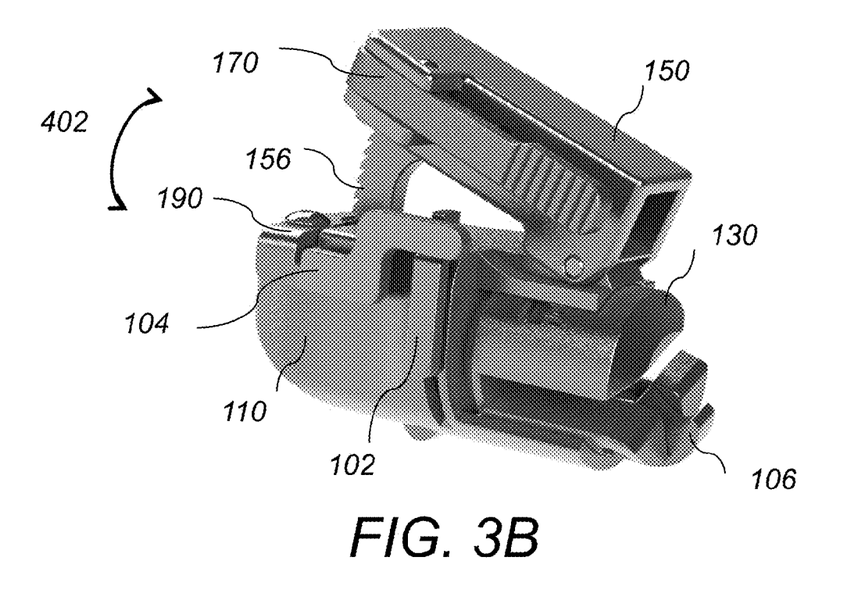
FIG. 3B is a perspective view of the three-dimensional tilt ratchet assembly of FIG. 3A in the tilted configuration and "open" position.
Figure 3C:
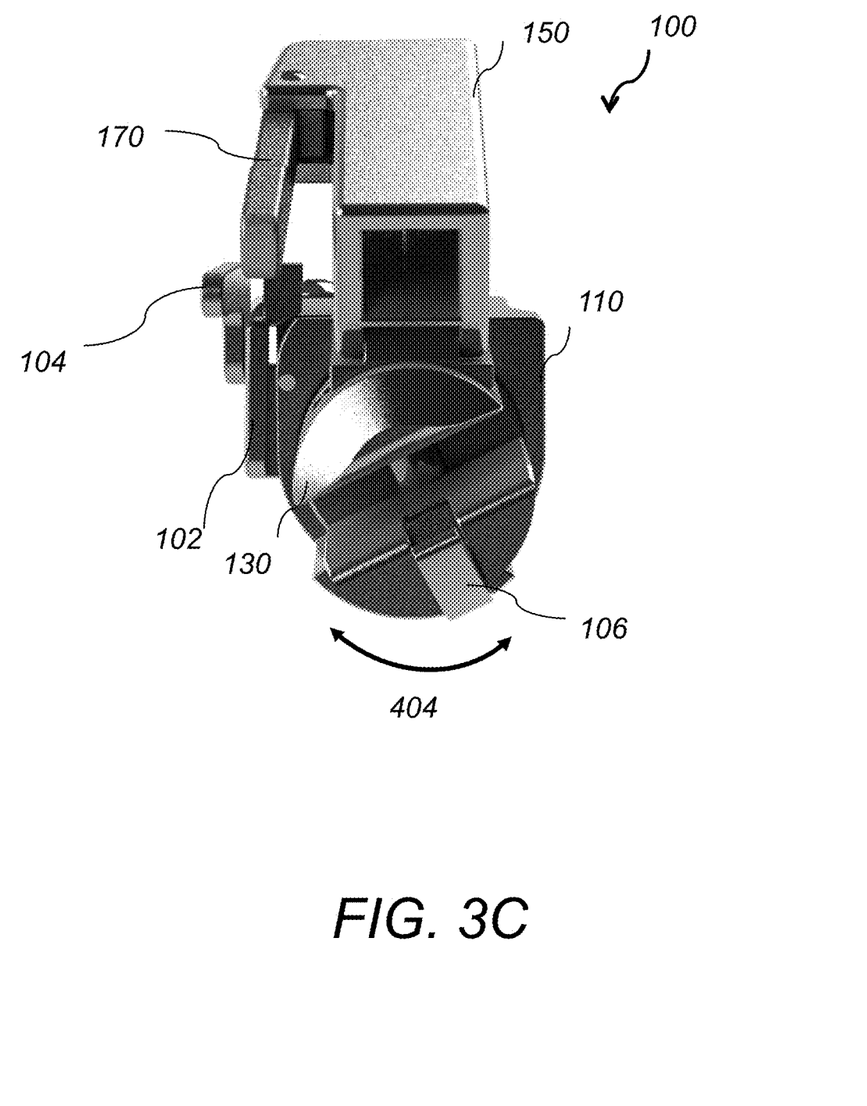
FIG. 3C is a front view of the three-dimensional tilt ratchet assembly of FIG. 3A in a rotated position.

Referring to FIG. 3A, FIG. 3B and FIG. 3C, retractor assembly 100 according to this invention includes a housing member 110, rotating indexer 130, and a refractor blade holder 150. Housing member 110 is configured to hold the rotating indexer 130 within a slot 112. Retractor blade holder 150 is pivotally connected to housing member 110 and is adapted to retain a retractor blade 18 with an attached elongate ratcheted stem 22 similar to the one depicted in FIG. 1. As the bidirectional arrow 406 suggests, the retractor blade 18 and attached elongate ratcheted stem 22 can be moved towards or away from the retractor blade holder 150 and fixed at this specific distance with lever 170. Refractor blade holder 150 can also be vertically pivoted up and down as indicated by the arrow 402, that is, towards or away from housing member 110 to change the vertical position of the retractor blade 18, and fixed in place with a ratchet release bar 190. Finally, rotating indexer 130 and housing member 110 are rotatable (as indicated by arrow 404) with respect to one another to effect angular adjustment of the retractor blade 18 and attached stem 22. Housing member 110 is rotatable about the longitudinal axis of rotating indexer 130.

In this embodiment, retractor assembly 100 further includes a spring loaded retention clip 106, a spring-loaded locking lever 104 and a spring loaded key 102. Spring loaded retention clip 106 includes a hook-shaped retention clip that is used to lock the position of the rotating indexer 130 and the entire retractor assembly 100 onto ring 16. Retention clip 106 is connected to the lower portion 130a of the rotating indexer 130 via a spring loaded hinge connection 107. Hinge connection 107 includes a pin 107a that is inserted within opening 109 formed in the front lower portion 130a of the rotating indexer 130 and within opening 108 formed in the back portion of clip 106, thereby providing a hinged connection between the rotating indexer 130 and ring 16, a shown in FIG. 4. Spring 107b forces the clip 106 to the open position when not locked in place. Opening and closing of retention clip 106 is activated by depressing the spring loaded locking lever 104, as will be described below.

Figure 4:
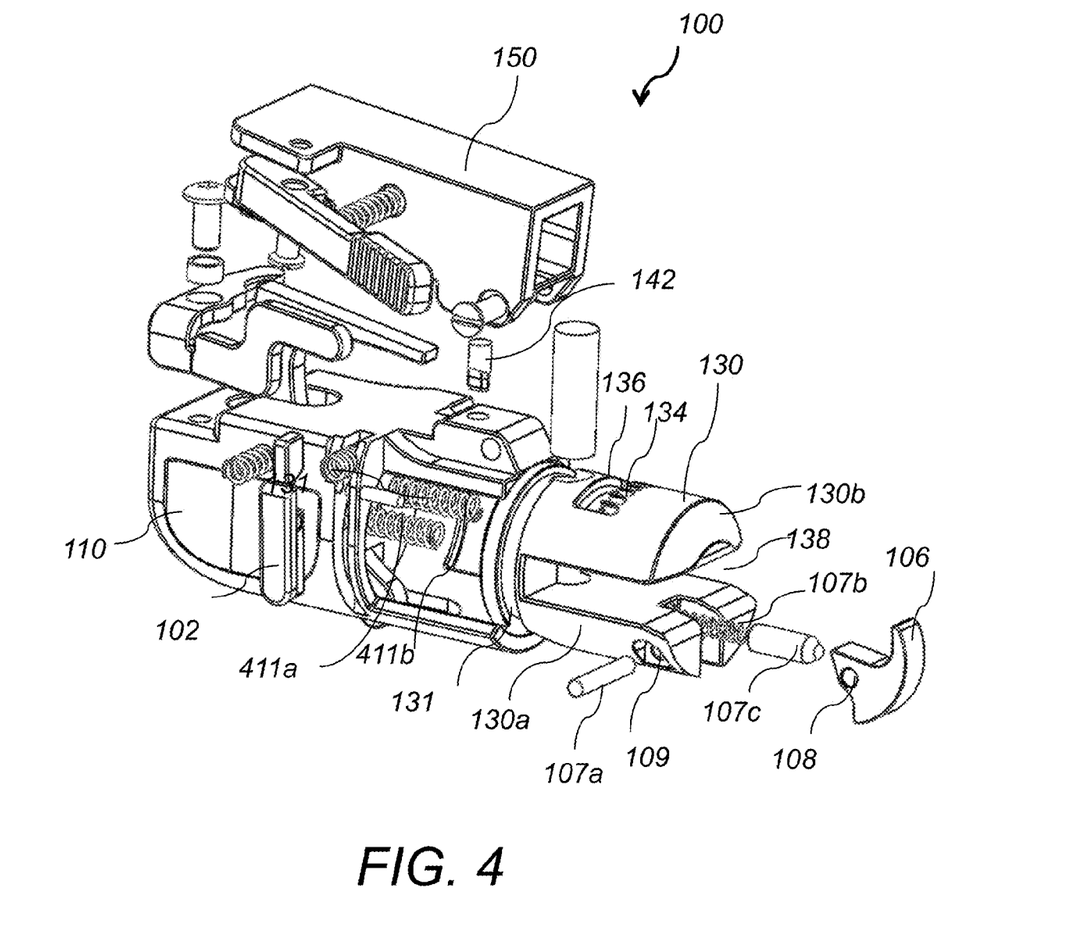
FIG. 4 is an exploded view of the three-dimensional tilt ratchet assembly of FIG. 3A.
Figure 5A:
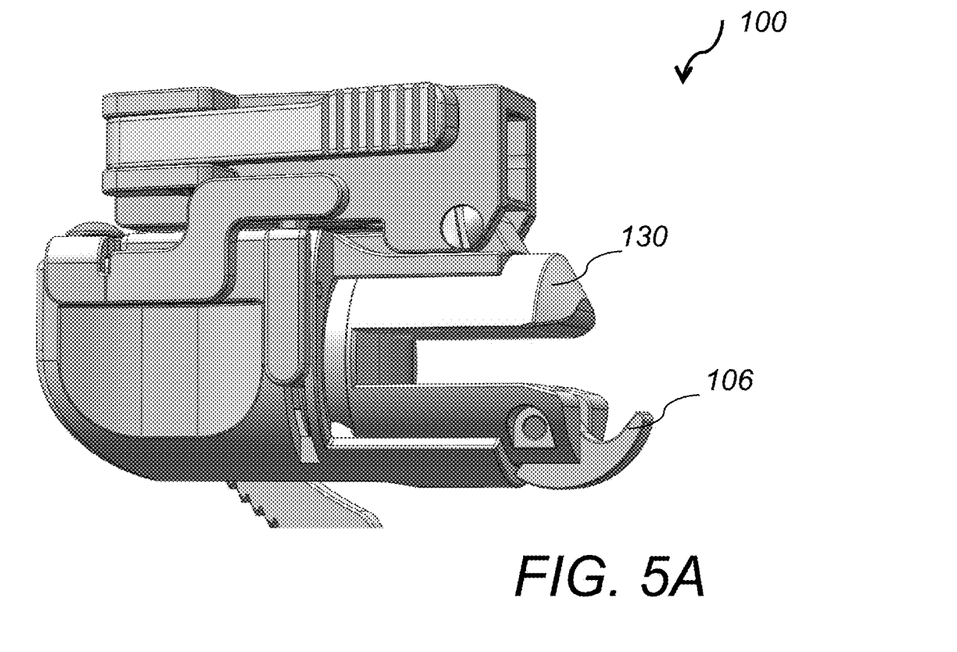
FIG. 5A is a side perspective view of the three-dimensional tilt ratchet assembly of FIG. 3A in the "open" position.
Figure 5B:
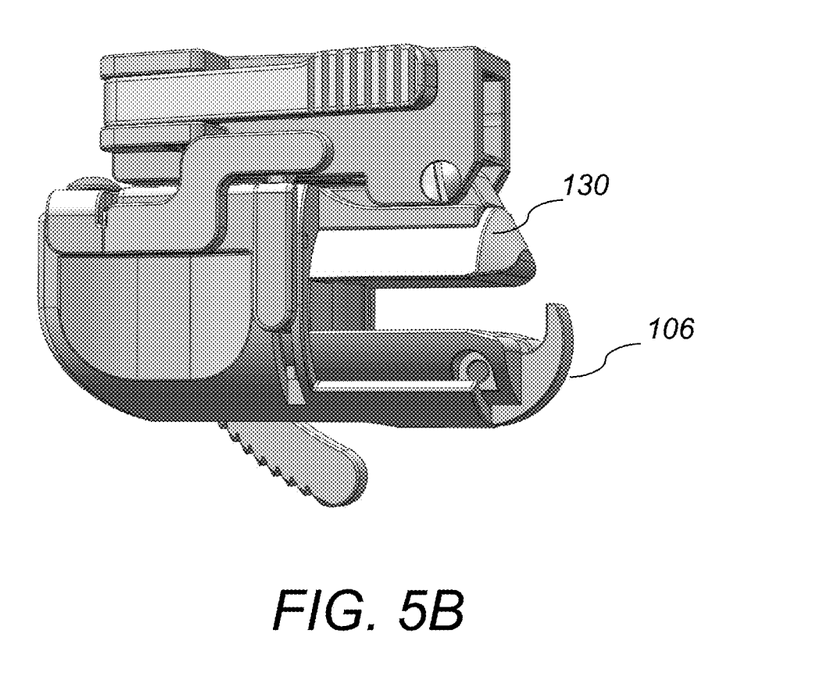
FIG. 5B is a side perspective view of the three-dimensional tilt ratchet assembly of FIG. 3A in the "closed" position.

Referring to FIG. 4, rotating indexer 130 includes a slot 138 that enables the ratchet mechanism 100 to be attached to the circumferential ring 16, a plurality of indents 134 that enable the housing member 110 to rotate about the rotating indexer 130 and maintain an angular position relative to the rotating indexer 130, and a circumferential slot 131.

Spring loaded lever key 102 falls into circumferential slot 131 when the rotating indexer 130 is pushed back into the housing member 110 and this locks the position of the rotating indexer 130 within the housing member 110. Once the spring loaded lever 104 is depressed, the lever key 102 is released and the rotating indexer 130 springs back into the open position and lowers the retention clip 106. Index pin 142 mates with the indents 134 on the rotating indexer and locks the angle between the rotating indexer and the housing member 110. Index pin 142 also maintains the open position of the rotating indexer.

Figure 6A:
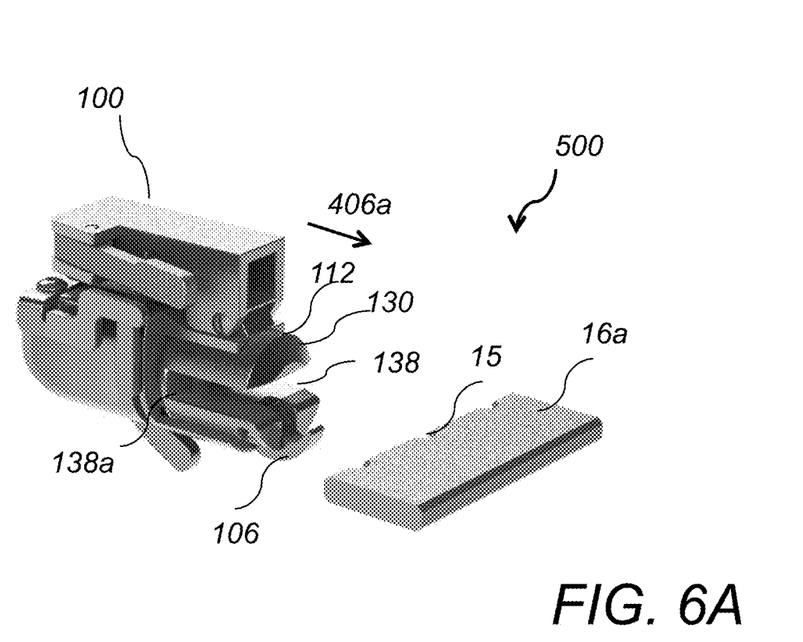
FIG. 6A-FIG. 6D depict the steps of bringing the three-dimensional tilt ratchet assembly of FIG. 3A in the "open" unlocked and "closed" locked positions around a support structure.
Figure 6B:
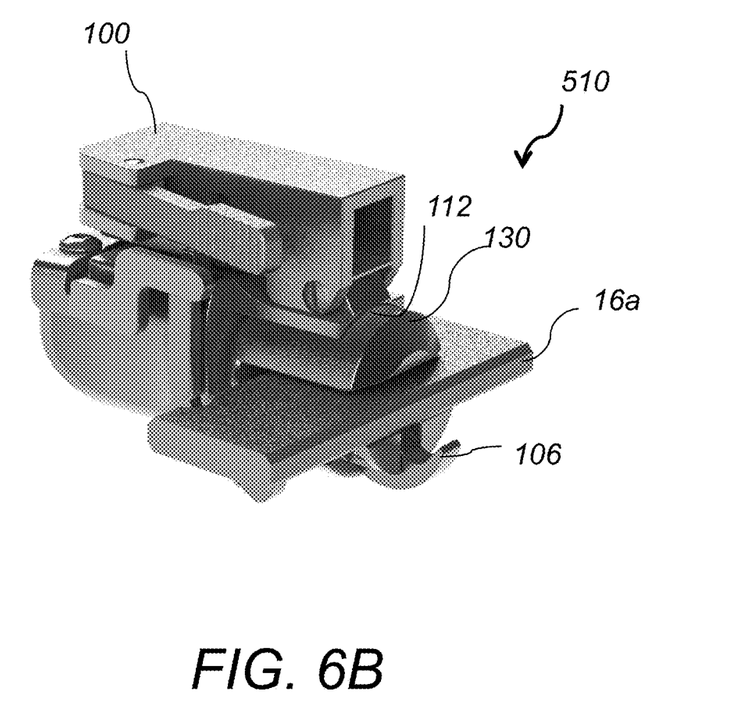
Figure 6C:
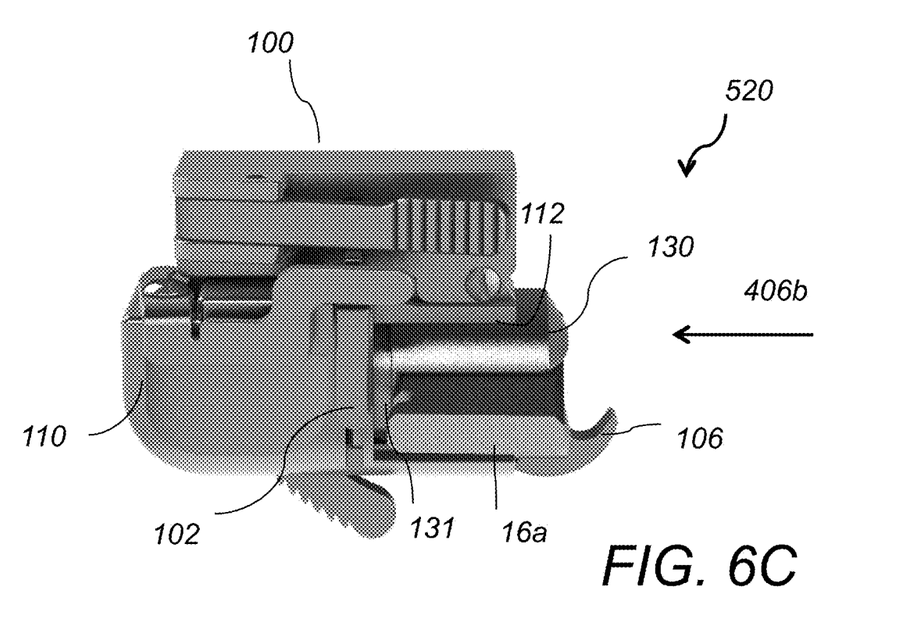
Figure 6D:
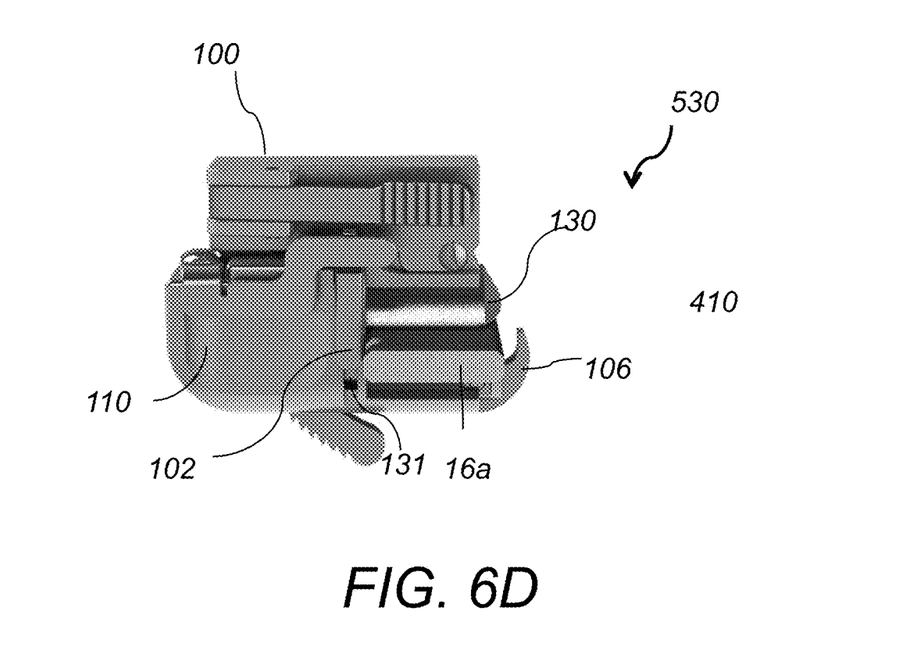
Figure 7:
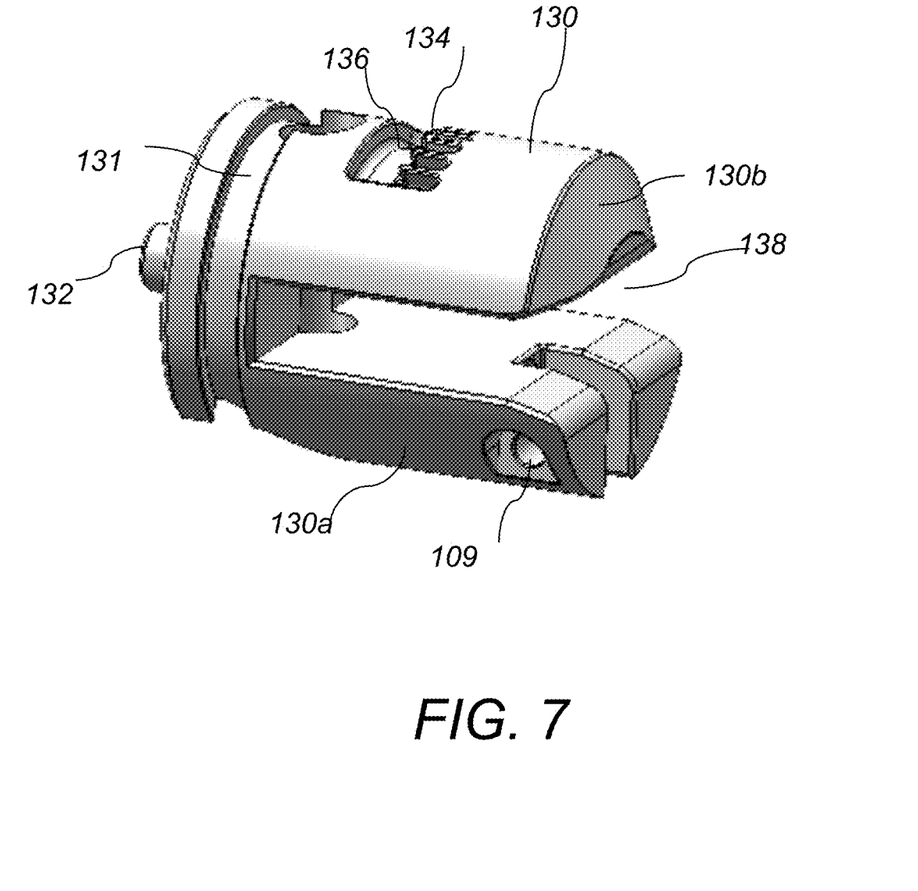
FIG. 7 depicts a perspective view of the rotating indexer of the three-dimensional tilt ratchet assembly of FIG. 3A.

In operation, rotating indexer 130 is extended in the "open" position, as shown in FIG. 6A. In this "open" position rotating indexer 130 slides forward along direction 406a out of opening 112 and is held open by springs 411a, 411b. In this configuration, retention clip 106 is also held open by spring 107b. Next, a mating component 16a of ring 16 is inserted into opening 138 of the rotating indexer 130, and is placed so that edge 15 of component 16a touches the back 138a of opening 138, as shown in FIG. 6B. Next, rotating indexer 130 and component 16a are pushed back into opening 112 along direction 406b, as shown in FIG. 6C. This motion of the rotating indexer 130 along direction 406b moves circumferential slot 131 toward the spring loaded lever key 102. Once, the lever key 102 of the spring loaded lever 104 falls into slot 131, the rotating indexer 130 and the entire ratchet 100 locks into the "closed" position, as shown in FIG. 6D. In this "closed" position, rotating indexer 130 is fully recessed into housing member 110 and the retention clip 106 is forced into the closed position, as shown in FIG. 6D. In the "closed" position, the housing member 110 can be rotated along arrow 404 and placed at an angle relative to the rotating indexer 130. As was mentioned above, the housing member can be rotated in increments of approximately 10 degrees up to about 30 degrees to the left or to the right (total of 60 degrees) with respect to the plane of the circumferential ring 16, to the left or right of plane perpendicular to midpoint of rotating indexer 130. The assembly is unlocked by pressing lever 104. Pressing lever 104 releases key 102 and simultaneously disengages springs 411a, 411b and 107b. Disengaging of springs 411a, 411b causes them to expand and push the rotating indexer 130 out of opening 112 along direction 406a. This brings rotating indexer 130 to the "open" position, where it is unlocked. Disengaging of spring 107b forces the clip 106 into open position.

Several embodiments of the present invention have been described. Nevertheless, it will be understood that various modifications may be made without departing from the spirit and scope of the invention. Accordingly, other embodiments are within the scope of the following claims.

What is claimed is:

1. A ratchet assembly for multi-dimensional movement and placement of a retractor blade comprising:
    a retractor blade holder shaped and dimensioned to receive a stem of a retractor blade, the retractor blade holder comprising a locking mechanism that enables selective lateral adjustment of the retractor blade relative to the retractor blade holder;
    a housing member to which the retractor blade holder is mated, wherein the retractor blade holder is vertically pivotable with respect to the housing member to enable selective vertical pivoting adjustment of the retractor blade relative to the housing member;
    a rotating indexer mated to the housing member, wherein the housing member is rotatable with respect to the rotating indexer so that the retractor blade holder, the housing member and the retractor blade are able to selectively rotate about the longitudinal axis of the rotating indexer, and wherein the rotating indexer is shaped and dimensioned to mount onto a rim of a surgical support; and
    a self-retaining locking mechanism that simultaneously locks or unlocks the position of the housing member relative to the rotating indexer and the position of the rotating indexer and the entire ratchet assembly onto the rim of the surgical support; and wherein the self retaining locking mechanism comprises a spring loaded lever, a spring loaded key and a spring loaded retention clip and wherein the spring loaded key interfaces with and engages a circumferential slot formed on the rotating indexer to lock the position of the housing member relative to the rotating indexer, and to lock the position of the rotating indexer and the entire ratchet assembly onto the rim of the surgical support with the spring loaded retention clip.

2. The ratchet assembly of claim 1, wherein depressing of the spring loaded lever disengages the spring loaded key from the circumferential slot and propels the rotating indexer forward and thereby simultaneously unlocks the position of the housing member relative to the rotating indexer, and unlocks the rotating indexer and the entire ratchet assembly from the rim of the surgical support by opening the spring loaded retention clip.

3. The ratchet assembly of claim 2, wherein the spring loaded retention clip comprises a hook-shaped clip that is shaped and dimensioned to lock the position of the rotating index and the entire ratchet assembly onto the rim of the surgical support and is connected to a front lower portion of the rotating indexer via a spring loaded hinge.

4. The ratchet assembly of claim 3, wherein the spring loaded hinge comprises a pin configured to be inserted within an opening formed in the front lower portion of the rotating indexer, and a spring.

5. The ratchet assembly of claim 2, wherein the self retaining locking mechanism further comprises a set of at least two springs and wherein the set of the at least two springs is activated when the spring loaded key disengages from the circumferential slot and the at least two springs propel the rotating indexer forward.

6. The ratchet assembly of claim 1, wherein the rotating indexer further comprises a slot shaped and dimensioned to enable the ratchet assembly to be attached to the rim of the surgical support, and a plurality of indents extending circumferentially about the rotating indexer and being shaped and dimension to set and maintain the angular position of the housing member relative to the rotating indexer.

7. The ratchet assembly of claim 6, wherein a locking pin extends from the housing member and engages one of the plurality of indents of the rotating indexer for maintaining the angular position of the housing member relative to the rotating indexer.

8. The ratchet assembly of claim 6, wherein the indents are arranged at increments of 10 to 30 degrees.

* * * * *